(12) United States Patent
Szewczyk et al.

(10) Patent No.: US 7,169,773 B2
(45) Date of Patent: Jan. 30, 2007

(54) COMPOUNDS

(75) Inventors: Jerzy Ryszard Szewczyk, Research Triangle Park, NC (US); Kelly H. Donaldson, Research Triangle Park, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 20 days.

(21) Appl. No.: 11/171,711

(22) Filed: Jun. 30, 2005

(65) Prior Publication Data

US 2006/0003991 A1  Jan. 5, 2006

Related U.S. Application Data

(60) Provisional application No. 60/584,925, filed on Jul. 1, 2004.

(51) Int. Cl.
- *C07D 403/14* (2006.01)
- *A61K 31/551* (2006.01)
- *A61P 3/04* (2006.01)

(52) U.S. Cl. .................. 514/213.01; 514/221; 540/518

(58) Field of Classification Search ................ 540/518; 514/221, 212.07, 213.01
See application file for complete search history.

(56) References Cited

FOREIGN PATENT DOCUMENTS

| WO | WO 95/28391 | 10/1995 |
| WO | WO 00/33658 | 6/2000 |

OTHER PUBLICATIONS

Tyle, Iontohoretic Devices for Drug Delivery, Pharmaceutical Research 3(6):318-326 (1986).

Henke et al., Optimiation of 3-(1*H*-Indazol-3-ylmethyl)-1,5-benzodiazepines as Potent, Orally Active CCK-A Agonists, J. Med. Chem 40:2706-2725 (1997).

*Primary Examiner*—Bruck Kifle
(74) *Attorney, Agent, or Firm*—Bonnie L. Deppenbrock

(57) ABSTRACT

The present invention provides a compound of formula I comprising:

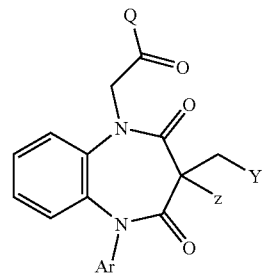

Formula 1 a pharmaceutically acceptable salt, solvate, or physiologically functional derivative thereof.

3 Claims, No Drawings

COMPOUNDS

CROSS REFERENCE TO RELATED APPLICATIONS

This application claims priority to U.S. Provisional Application No. 60/584,925 filed on Jul. 1, 2004, which is incorporated herein by reference in its entirety.

FIELD OF THE INVENTION

This invention relates to novel benzodiazepines that functions as agonists at the melanocortin 4 receptor (MC4R), to pharmaceutical compositions containing them, to processes for their preparation, and to their use in the treatment of diseases or conditions mediated by melanocortin 4 receptor (MC4R) including obesity, pain, diabetes, depression, anxiety, male and female sexual dysfunction and inflammation.

BACKGROUND OF THE INVENTION

Obesity is a medical condition that is reaching epidemic proportions among humans in a number of countries throughout the world. It is a condition that is also associated with or induces other diseases or conditions that disrupt life activities and lifestyles. Obesity is recognized as a serious risk factor for other diseases and conditions such as diabetes, anxiety, depression, hypertension, inflammation, cancer and arteriosclerosis. It is also known that increased body weight due to obesity can place a burden on joints, such as knee joints, causing arthritis, pain, and stiffness. It can contribute to elevated levels of cholesterol in the blood. Because overeating and obesity have become such a problem in the general population, many individuals are now interested in losing weight, reducing weight, and/or maintaining a healthy body weight and lifestyle.

Pro-opiornelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism.

A specific single MC-R that may be targeted for the control of obesity has not yet been identified. To date five distinct MC-R's have been identified, and these are expressed in different tissues. MC-1R is mainly expressed in melanocytes. MC-2R is expressed in the adrenal gland. MC-3R is expressed in the brain, gut, and placenta and may be involved in the control of food intake and thermogenesis. MC-4R is uniquely expressed in the brain, and its inactivation was shown to cause obesity. Evidence has been presented that MC-4R signaling is important in mediating feed behavior. MC-5R is expressed in many tissues, including white fat, placenta, and exocrine glands. A low level of expression of MC-5R is also observed in the brain.

WO 95/28391 discloses CCK or gastrin modulating 1,5 benzodiazepine derivatives, intermediates, pharmaceutical compositions for treating obesity, gall bladder stasis, disorders of pancreatic secretion, methods for treatment and processes for preparing 1,5 benzodiazepine compounds. This reference discloses 1,5-benzodiazepine compounds as CCK-A agonist activity associated with obesity and/or weight loss. This reference does not appreciate that specific benzodiazepines may provide melanocortin-4 agonist activity.

WO 00/33658 discloses methods and compositions for treating a variety of disorders associated with or caused by undesirable body weight, including obesity as well as "wasting disorders." This reference discloses methods for identification of compounds that preferentially bind to and/or activate peripheral melanocortin receptors and which minimize binding and/or activation of central melanocortin receptors.

There is an on-going need for the development of a melanocortin 4 receptor agonist useful in the treatment of obesity and other associated or related diseases and conditions.

Accordingly, there is provided a novel group of benzodiazepines that exhibit a useful profile of activity as agonists of the MC4 receptor (i.e., MC4R agonist activity). Novel compounds of the invention are useful in the treatment of obesity and other associated diseases and conditions associated with obesity and other diseases/conditions mediated by the MC4 receptor.

SUMMARY OF THE INVENTION

The present invention provides a compound of Formula 1

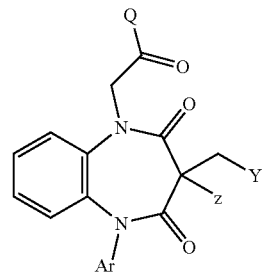

Formula 1 or a pharmaceutically acceptable salt, solvate, or physiologically functional derivative thereof, wherein:

Ar is aryl or heteroaryl having 5-14 ring members, each of which may be optionally substituted by one to four substituents each of which is independently selected from $C_{1-6}$alkyl, $C_{1-6}$alkenyl, halo, amino, $C_{1-6}$alkylamino, $C_{1-6}$dialkylamino, hydroxy, $C_{1-6}$alkoxy, $C_{1-6}$haloalkoxy, $C_{1-6}$haloalkyl, cyano or $C_{1-6}$alkylsulfonyl;

Z is —H or a $C_1$–$C_6$alkoxy;

Q is selected from the group consisting of

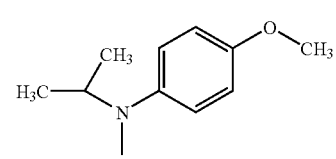

-continued
and

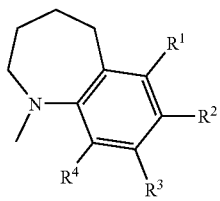

wherein O, each $R^1$, $R^2$, $R^3$, and $R^4$ is independently selected from the group consisting of hydrogen, a $C_1$–$C_6$alkyl, a $C_1$–$C_6$alkoxy, and hydroxy;
Y is selected from the group consisting of

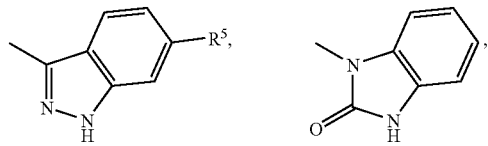

and

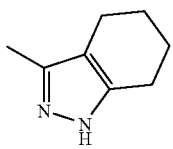

wherein $R^5$ is selected from hydrogen and fluorine with the proviso that the compound is not racemic 2-[2,4-Dioxo-3-(1H-indazol-3-ylmethylene)-3-methoxy-5-(3-pyridyl)-2,3,4,5-tetrahydro-1H-1,5-benzodiazepin-1-yl]-N-isopropyl-N-(4-methoxyphenyl)acetamide.

In a second aspect there is provided a compound of formula 1, a physiologically acceptable salt, solvate, or physiologically functional derivative thereof for use in therapy.

In another aspect of the invention, there is provided a pharmaceutical composition comprising a compound of Formula 1, a physiologically acceptable salt, solvate, or physiologically functional derivative thereof and one or more pharmaceutically acceptable carriers; dilutents and excipients.

In a fourth aspect of the present invention, there is provided a method of treating a disorder in a mammal, said disorder being mediated by MC4R, comprising: administering to said mammal a therapeutically effective amount of a compound of formula (I) or a salt, solvate or a physiologically functional derivative thereof.

In a fifth aspect, there is provided a method for treating obesity, diabetes, inflammation, depression, male and female sexual dysfunction and anxiety, which method comprises the administration to a mammal, including a human, of a therapeutically effective amount of a compound of Formula 1, a salt, solvate, or physiological derivative thereof.

In a sixth aspect of the present invention, there is provided the use of a compound of formula (I), or a salt, solvate, or a physiologically functional derivative thereof in the preparation of a medicament for use in the treatment of a disorder mediated by MC4R.

In a seventh aspect, there is provided the use of a compound of formula (I), or a salt, solvate, or a physiologically functional derivative thereof in the preparation of a medicament for use in the treatment of obesity, diabetes, inflammation, depression, male and female sexual dysfunction and anxiety.

In still a further aspect of the invention there is provided processes for the preparation of a compound of Formula 1, a physiologically acceptable salt, solvate or a physiologically functional derivative thereof.

DETAILED DESCRIPTION OF THE INVENTION

As used herein, "a compound of the invention" or "a compound of Formula 1" means a compound of Formula 1 or a pharmaceutically acceptable salt, solvate, or physiologically functional derivative (such as, e.g., a prodrug), thereof.

As used herein, the term "optionally" means that the subsequently described event(s) may or may not occur, and includes both event(s) that occur and events that do not occur.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing prevention, or amelioration of a disease, disorder, or side effect, or a decrease in the rate of advancement of a disease or disorder. The term also includes within its scope amounts effective to enhance normal physiological function.

As used herein, unless otherwise specified, the term "alkyl" and "alkylene" refer to straight or branched chain hydrocarbyl radical containing the specified number of carbon atoms. Examples of "alkyl" as used herein include, but are not limited to, methyl, ethyl, n-propyl, n-butyl, n-pentyl, isobutyl, isopropyl, tert-butyl, and hexyl.

As used herein, unless otherwise specified, the term "alkenyl" refers to straight or branched hydrocarbon chains containing the specified number of carbon atoms and at least one and up to three carbon-carbon double bonds. Examples of "alkenyl" as used herein include, but are not limited to, ethenyl and propenyl.

Unless otherwise specified, the term "aryl", as used herein, refers to monocyclic carbocyclic groups and fused bicyclic carbocyclic groups having the specified number of ring atoms and having at least one aromatic ring. Examples of particular aryl groups include, but are not limited to, phenyl and napthyl.

The term "heteroaryl", unless otherwise specified, refers to aromatic monocyclic groups and aromatic fused bicyclic groups having at least one aromatic ring having the specified number of ring members (e.g., carbon and heteroatoms N, O, and/or S) and containing 1, 2, 3, or 4 heteroatoms selected from N, O, and S. Examples of particular heteroaryl groups include, but are not limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, benzazepine, benzimidazole, benzoximidazole, indole, oxindole and indazole.

As used herein, the terms "$C_{1-6}$haloalkyl" refers to an alkyl group as defined above containing at least 1, and at most 6 carbon atoms respectively substituted with at least one halo group, halo being as defined herein. Examples of such branched or straight chained haloalkyl groups useful in the present invention include, but are not limited to methyl, ethyl, propyl, isopropyl, isobutyl and n-butyl substituted independently with one or more halos, eg. fluoro, chloro, bromo and iodo.

As used herein, the term "alkoxy" refers to the group RaO—, where Ra is alkyl as defined above and the terms "$C_1$–$C_3$alkoxy" and "$C_1$–$C_6$alkoxy" refer to an alkoxy group as defined herein wherein the alkyl moiety contains at least 1, and at most 3 or 6, carbon atoms. Exemplary "$C_1$–$C_3$alkoxy" and "$C_1$–$C_6$alkoxy" groups useful in the present invention include, but are not limited to methoxy, ethoxy, n-propoxy, isopropoxy, n-butoxy, and t-butoxy.

As used herein, the term "amino" refers to the group —$NH_2$.

As used herein the term "alkylamino" refers to the group —NHRa wherein Ra is alkyl as defined.

As used herein, the term "haloalkoxy" refers to the group RaO—, where Ra is haloalkyl as defined above and the term "$C_1$–$C_6$haloalkoxy" refers to a haloalkoxy groups as defined herein wherein the haloalkyl moiety contains at least 1, and at most 6, carbon atoms. Exemplary $C_1$–$C_6$haloalkoxy groups useful in the present invention include, but is not limited to, trifluoromethoxy.

As used herein, the term "alkylsulfanyl" refers to the group RaS—, where Ra is alkyl as defined above and the terms "$C_1$–$C_6$alkylsulfanyl" refers to an alkylsulfanyl group as defined herein wherein the alkyl moiety contains at least 1, and at most 6, carbon atoms.

As used herein, the term "cyano" refers to the group —CN.

Preferably Ar represents phenyl or 2, 3 or 4 pyridyl group, each of which may be optionally substituted by one to four substituents each independently selected from halo, $C_1$–$C_3$alkoxy or $C_1$–$C_3$alkyl. Most preferred are chloro, fluoro and methoxy. More preferably Ar represents a phenyl or 2-, 3-, or 4-, pyridyloptionally substituted with at least one halo and/or methoxy group. Preferably Ar is phenyl or 3-pyridyl. Most preferably Ar is phenyl.

Preferably, each $R^1$, $R^2$, $R^3$, and $R^4$ is independently selected from the group consisting of hydrogen (—H), methyl (—$CH_3$), methoxy (—$OCH_3$), and hydroxy (—OH).

Preferably Z is hydrogen (—H) or $C_1$–$C_6$-or methoxy.

Additionally, in a preferred embodiment of Formula 1, when Z is methoxy, Q is

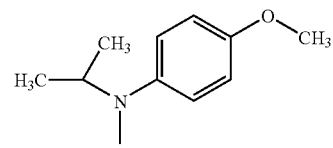

Two most preferred compounds in accordance with Formula 1 are

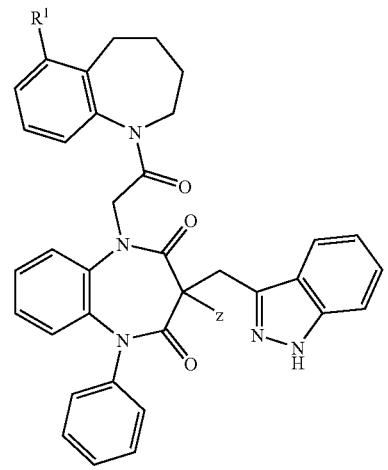

and

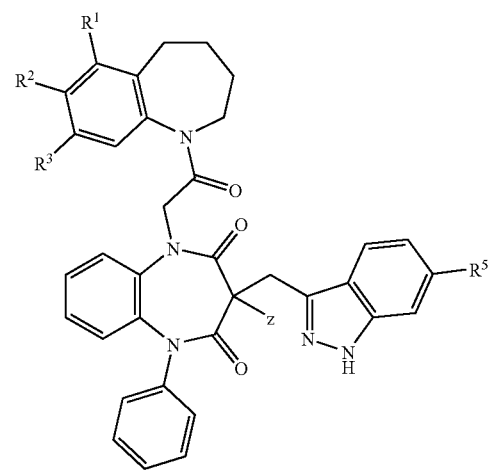

While the preferred groups for each variable have generally been listed above separately for each variable, preferred compounds of this invention include those in which several or each variable in Formula (1) is selected from the preferred, more preferred, or most preferred groups for each variable. Therefore, this invention is intended to include all combinations of preferred, more preferred, and most preferred groups.

Specific compounds of Formula 1 include, but are not limited to, those set forth in Table 1 below and/or those prepared in the examples herein.

TABLE 1

Illustrative Compounds of the Invention

| Example # | Structure | Name |
|---|---|---|
| 1 | 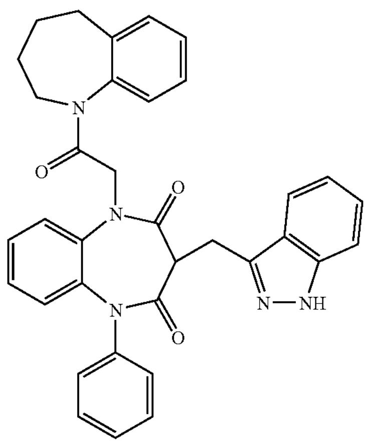 | 3-(1H-indazol-3-ylmethylene)-5-phenyl-1-[2-(2,3,4,5-tetrahydro-1H-1-benzazepin-1-yl)-2-oxoethyl]-1H-1,5-benzodiazepine-2,4-dione |
| 2 | 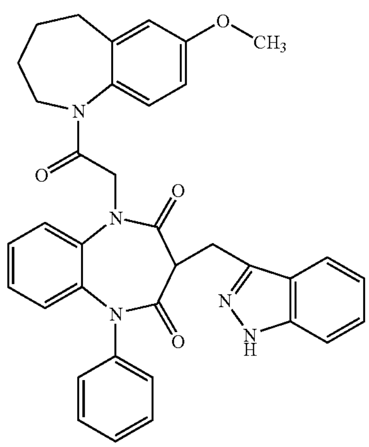 | 3-(1H-indazol-3-ylmethylene)-1-[2-(7-methoxy-2,3,4,5-tetrahydro-1H-1-benzazepin-1-yl)-2-oxoethyl]-5-phenyl-1H-1,5-benzodiazepine-2,4-dione |
| 3 | 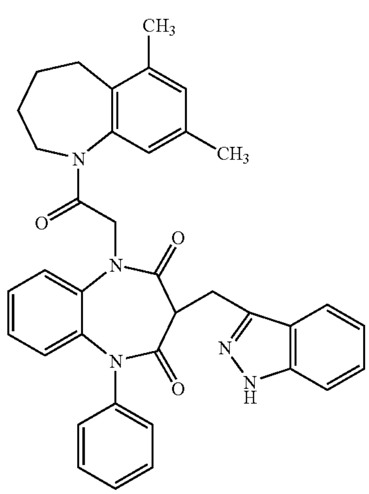 | 1-[2-(6,8-dimethyl-2,3,4,5-tetrahydro-1H-1-benzazepin-1-yl)-2-oxoethyl]-3-(1H-indazol-3-ylmethylene)-5-phenyl-1H-1,5-benzodiazepine-2,4-dione<br>3 is a racemate |

TABLE 1-continued

Illustrative Compounds of the Invention

| Example # | Structure | Name |
|---|---|---|
| 4 | 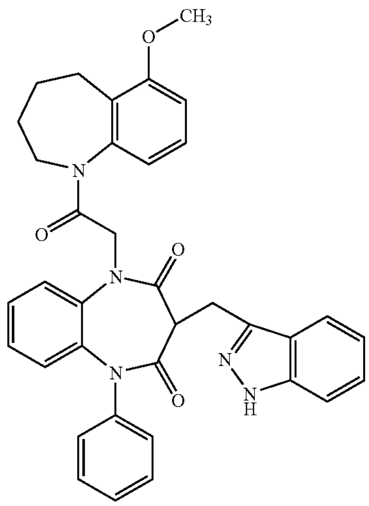 | 3-(1H-indazol-3-ylmethylene)-1-[2-(6-methoxy-2,3,4,5-tetrahydro-1H-1-benzazepin-1-yl)-2-oxoethyl]-5-phenyl-1H-1,5-benzodiazepine-2,4-dione<br>4 is a racemate |
| 5 | 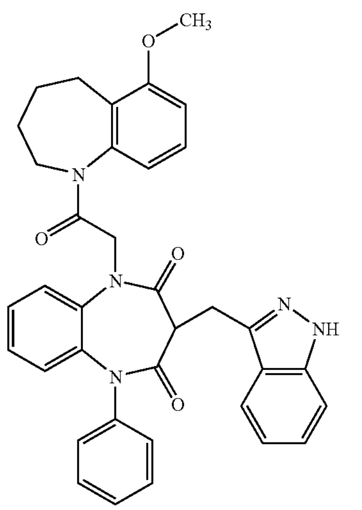 | (3R)-3-(1H-indazol-3-ylmethylene)-1-[2-(6-methoxy-2,3,4,5-tetrahydro-1H-1-benzazepin-1-yl)-2-oxoethyl]-5-phenyl-1H-1,5-benzodiazepine-2,4-dione<br>5 is a (3R)-chiral enantiomer of 4 |
| 6 | 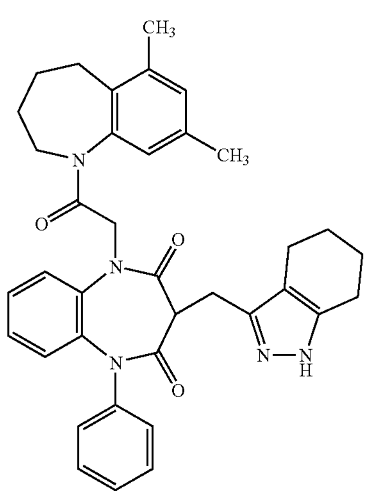 | (3R)-1-[2-(6,8-dimethyl-2,3,4,5-tetrahydro-1H-1-benzazepin-1-yl)-2-oxoethyl]-5-phenyl-3-(4,5,6,7-tetrahydro-1H-indazol-3-ylmethylene)-1H-1,5-benzodiazepine-2,4-dione<br>6 is a (3R)-chiral enantiomer of 3 |

TABLE 1-continued

Illustrative Compounds of the Invention

| Example # | Structure | Name |
|---|---|---|
| 7 | 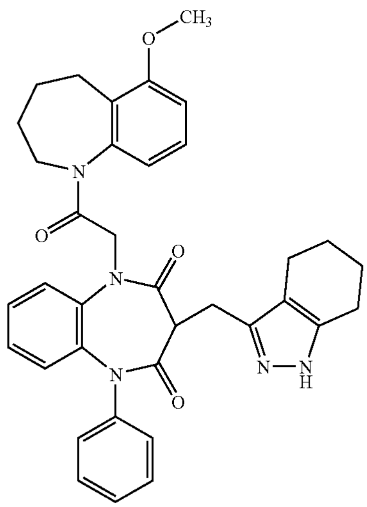 | (3R)-1-[2-(6-methoxy-2,3,4,5-tetrahydro-1H-1-benzazepin-1-yl)-2-oxoethyl]-5-phenyl-3-(4,5,6,7-tetrahydro-1H-indazol-3-ylmethylene)-1H-1,5-benzodiazepine-2,4-dione |
| 8 | 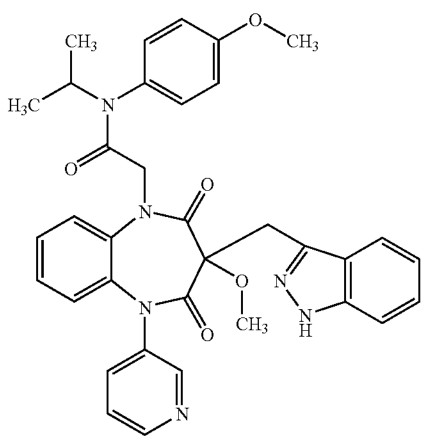 | 2-[2,4-dioxo-3-(1H-indazol-3-ylmethylene)-3-methoxy-5-(3-pyridyl)-2,3,4,5-tetrahydro-1H-1,5-benzodiazepin-1-yl]-N-isopropyl-N-(4-methoxyphenyl)acetamide (a racemate) |
| 9 | 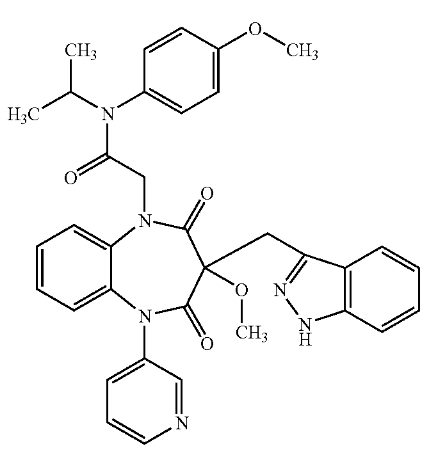 | 2-[2,4-dioxo-3-(1H-indazol-3-ylmethylene)-3-methoxy-5-(3-pyridyl)-2,3,4,5-tetrahydro-1H-1,5-benzodiazepin-1-yl]-N-isopropyl-N-(4-methoxyphenyl)acetamide ENANTIOMER 1 of COMPOUND 8 |

TABLE 1-continued

Illustrative Compounds of the Invention

| Example # | Structure | Name |
|---|---|---|
| 10 | 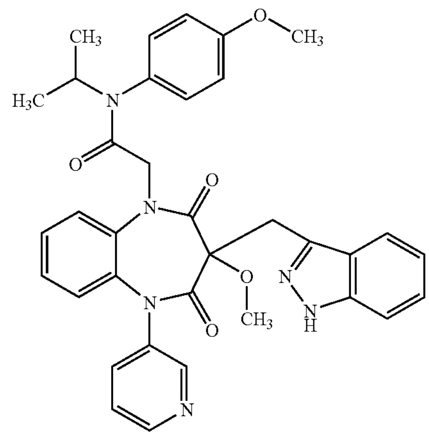 | 2-[2,4-dioxo-3-(1H-indazol-3-ylmethylene)-3-methoxy-5-(3-pyridyl)-2,3,4,5-tetrahydro-1H-1,5-benzodiazepin-1-yl]-N-isopropyl-N-(4-methoxyphenyl)acetamide ENANTIOMER 2 of COMPOUND 8 |
| 11 | 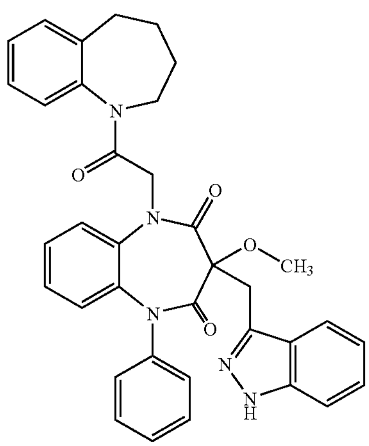 | 3-(1H-indazol-3-ylmethylene)-3-methoxy-5-phenyl-1-[2-(2,3,4,5-tetrahydro-1H-1-benzazepin-1-yl)-2-oxoethyl]-1H-1,5-benzodiazepine-2,4-dione |
| 12 | 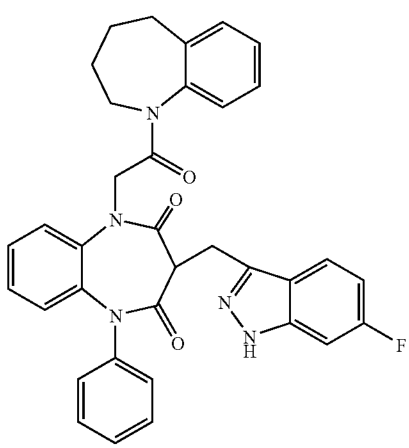 | 3-(6-fluoro-1H-indazol-3-ylmethylene)-5-phenyl-1-[2-(2,3,4,5-tetrahydro-1H-1-benzazepin-1-yl)-2-oxoethyl]-1H-1,5-benzodiazepine-2,4-dione |

Certain compounds of Formula 1 may exist in stereoisomeric forms (e.g., they may contain one or more asymmetric carbon atoms or may exhibit cis-trans isomerism). The individual stereoisomers (enantiomers and diasteromers) and mixtures of these are included within the scope of the present invention. The present invention also covers the individual isomers of the compounds represented by Formula 1 as well as mixtures with isomers thereof in which one or more chiral centers are inverted. Certain compounds of Formula 1 may be prepared as regioisomers. The present invention covers both the mixture of regioisomers as well as individual compounds. When a compound of formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Likewise, it is understood that compounds of Formula 1 may exist in tautomeric forms other than that shown in the formula and these are also included within the scope of the present invention. It is to be understood that the present invention includes all combinations and subsets of the particular groups defined herein above.

It will be appreciated by those skilled in the art that the compounds of the present invention may also be utilized in the form of a pharmaceutically acceptable salt, solvate or physiologically functional derivative thereof (e.g., a prodrug).

It will be appreciated by a person skilled in the art that the compounds of the invention may be utilised in the form of a pharmaceutically acceptable salt, solvate or physiologically functional derivative thereof.

As used herein, the term "solvate" refers to a complex of variable stoichiometry formed by a solute (in this invention, a compound of formula (I) or a salt or physiologically functional derivative thereof and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acide. Most preferably the solvent used is water.

It will also be appreciated by those skilled in organic chemistry that many organic compounds can exist in more than one crystalline form. For example, crystalline form may vary from solvate to solvate. Thus, all crystalline forms of the compounds of formula (I) or the pharmaceutically acceptable solvates thereof are within the scope of the present invention.

The term "physiologically functional derivative" as used herein refers to any pharmaceutically acceptable derivative of a compound of the present invention, for example, a ester or an amide of a compound of Formula 1, which upon administration to an animal, particularly a mammal, such as a human, is capable of providing (directly or indirectly) a compound of the present invention or an active metabolite thereof. See, for example, *Burger's Medicinal Chemistry and Drug Discovery*, 5$^{th}$ Edition, Vol. 1: Principles and Practice.

Processes for preparing pharmaceutically salts, solvates, and physiologically functional derivatives of the compounds of Formula 1 are conventional in the art. See, for example, *Burger's Medicinal Chemistry and Drug Discovery*, 5$^{th}$ Edition, Vol. 1: Principles and Practice.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropyl-methacrylamide-phenol, polyhydroxyethylasparta-midephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 200 mg/kg body weight of recipient (mammal) per day and more usually in the range of 1 to 100 mg/kg body weight per day. Thus, for a 70 kg adult mammal, the actual amount per day would usually be from 70 mg to 7 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

Compounds of Formula 1 are believed to have a role in the treatment of MC4R mediated diseases. As used herein, the term "treatment" refers to alleviating a specified condition or disease, eliminating or reducing the symptoms of such condition or disease, slowing or eliminating the progression of the disease or condition, and/or preventing or delaying the reoccurrence of the condition or disease in a patient or subject.

Compounds of the present invention are agonists of melanocortin-4 and/or melanocortin-1 receptors and can be used for the treatment of a disease caused by or attributable to a POMC and/or MC4R activities. Accordingly, compounds of the invention may reduce hunger, suppress appetite, control eating, and/or induce satiety. Therefore, the present invention provides methods for the treatment of several conditions or diseases such as obesity, diabetes, inflamation, pain, depression (e.g., major depression and/or bipolar disorder), male and female sexual dysfunction and/or anxiety.

Such treatment comprises the administration of a therapeutically effective amount of a compound of Formula 1, preferably in the form of a salt, solvate, or physiologically functional derivative thereof to a mammal, especially a human. As used herein, the term "therapeutically effective amount" means an amount of a compound of Formula 1 which is sufficient, in the patient (mammal) to which it is administered, to elicit a biological or medical response in a cell, cell culture, animal or cell tissue, biological system, animal (including human) that is being sought, for instance by a researcher, clinician, or physician.

The present invention thus also provides compounds of formula (I) and pharmaceutically acceptable salts or solvates thereof, or physiologically functional derivatives thereof, for use in medical therapy, and particularly in the treatment of disorders mediated by MC4R.

The present invention is directed to methods of regulating, modulating, or inhibiting MC4R for the prevention and/or treatment of disorders related to MC4R. In particular, the compounds of the present invention can also be used in the treatment of obesity, diabetes, inflamation, pain, male and female sexual dysfunction, depression (e.g., major depression and/or bipolar disorder), and/or anxiety.

A further aspect of the invention provides a method of treatment of a mammal suffering from a disorder mediated by MC4R, which includes administering to said subject an effective amount of a compound of formula (I) or a pharmaceutically acceptable salt, solvate, or a physiologically functional derivative thereof. In a preferred embodiment, the disorder is a susceptible cancer.

A further aspect of the present invention provides the use of a compound of formula (I), or a pharmaceutically acceptable salt or solvate thereof, or a physiologically functional derivative thereof, in the preparation of a medicament for the treatment of a disorder mediated by MC4R.

The compounds for formula (I) for use in the instant invention may be used in combination with one or more other therapeutic agents for example, compounds employed in the treatment of diabetes, obesity, arteriosclerosis and/or hypertension. The compounds of the invention may also be used in combination with therapeutic agents useful in pain and/or inflammation. Further combinations include combinations with a diuretic fiber of anti-emetics. The invention thus provides in a further aspect the use of a combination comprising a compound of formula (I) with a further therapeutic agent in the treatment of MC4R mediated diseases.

When the compounds of formula (I) are used in combination with other therapeutic agents, the compounds may be administered either sequentially or simultaneously by any convenient route.

The combinations referred to above may conveniently be presented for use in the form of a pharmaceutical formulation and this pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same disease, the dose of each compound may differ from that when the compound is used alone. Appropriate doses will be readily appreciated by those skilled in the art.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I). Those skilled in the art will recognize if a stereocenter exists in compounds of Formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of Formula I can be prepared according to the synthetic sequences illustrated in Schemes detailed below and further detailed in the Examples section following.

Unless otherwise stated, Ar, Q, Z, R, $R^1$, $R^2$, $R^3$, $R^4$, and $R^5$ are as defined in Formula 1.

Preparation of Compounds of Formula 1

Compounds of Formula 1 are conveniently prepared in accordance with the reaction schemes and/or processes outlined or described below. As will be apparent to those skilled in the art, in the processes described below for the preparation of compounds of Formula 1, certain intermediates, may be in the form of pharmaceutically salts, solvates or physiologically functional derivatives of the compound. Those terms as applied to any intermediate employed in the process of preparing compounds of Formula 1 have the same meanings as noted above with respect to compounds of Formula 1. Processes for preparing pharmaceutically acceptable salts, solvates and physiologically functional derivatives of such intermediates are known in the art and are analogous to the process for preparing pharmaceutically acceptable salts, solvates and physiological functional derivatives of the compounds of Formula 1. Unless otherwise stated, Ar, Q, Z, R, $R^1$, $R^2$, $R^3$, $R^4$, and $R^5$ are as defined in Formula 1. In the schemes, particular Q and Y groups are illustrated but it would be apparent that compounds of Formula 1 with alternative Q and Y groups may be prepared by methods apparent to a skilled person.

First Preparation

Method A Compounds of Formula 1 can be prepared in accordance with Reaction Schematic 1 set forth below. Thus, compounds of Formula 1 may be prepared by reaction of tetralone with hydroxylamine yielding oxime (a), which could be either directly by reaction with DIBAL or by two step conversion with phosphoric acid followed by LiAlH$_4$ transformed to benzoazepine (b). Benzoazepine (b) is reacted with bromoacetylbromide yielding bromocetamide (c), which in reaction with N-arylphenylenediamine provided compound (d). Subsequent cyclization with malonyl dichloride afforded benzodiazepinedione (e). Alkylation with bromomethyl indazole provided benzodiazepine (f) which upon treatment with acid gave compound of Formula I. Compound of formula I or benzodiazepine (f) could be separated to afford enantiomers. Alternatively benzodiazepine (f) can be separated into two enantiomers and treatment with acid provides active enantiomer of compound of formula 1. Inactive enantiomer of benzodiazepine (f) can be racemize and separated again.

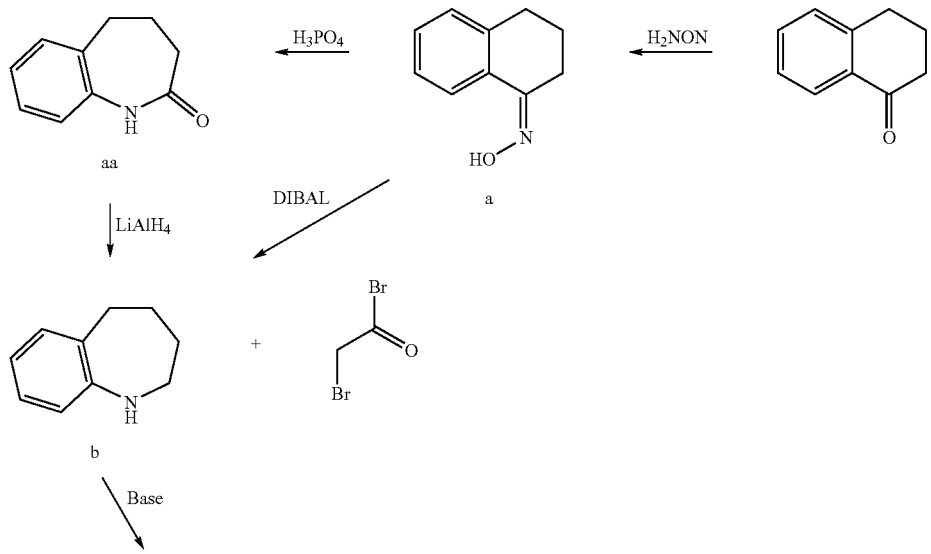

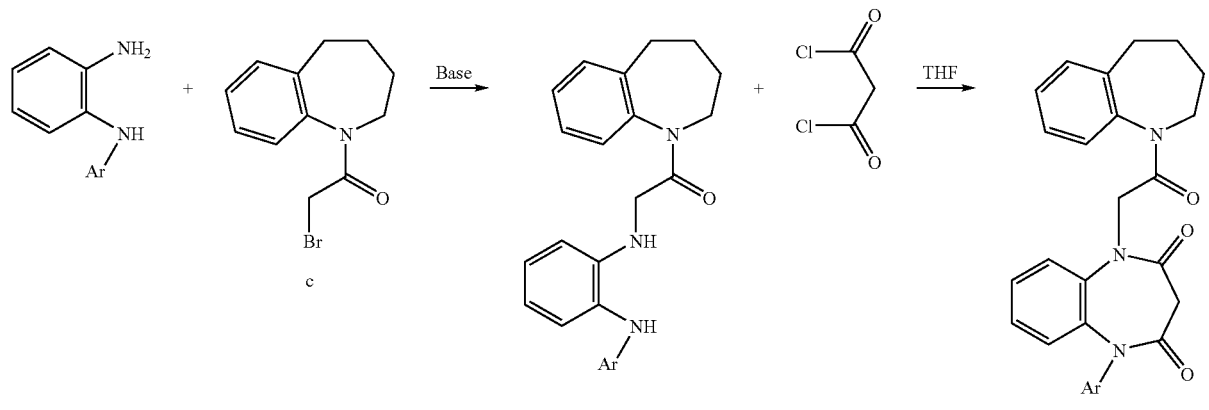

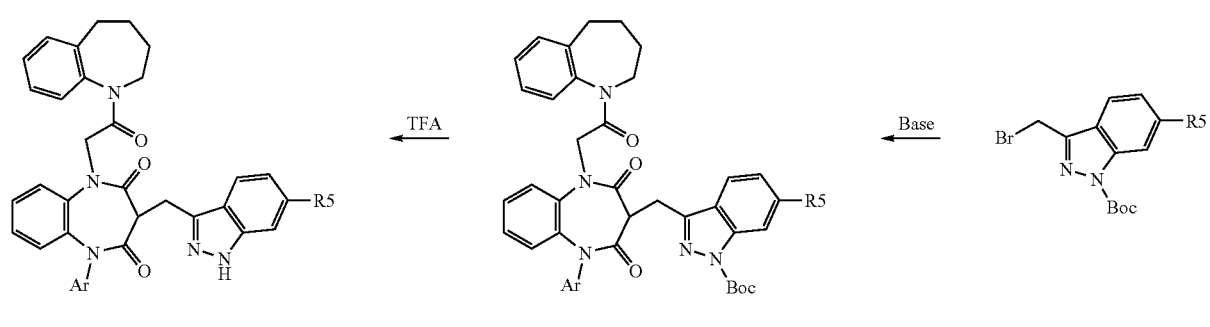

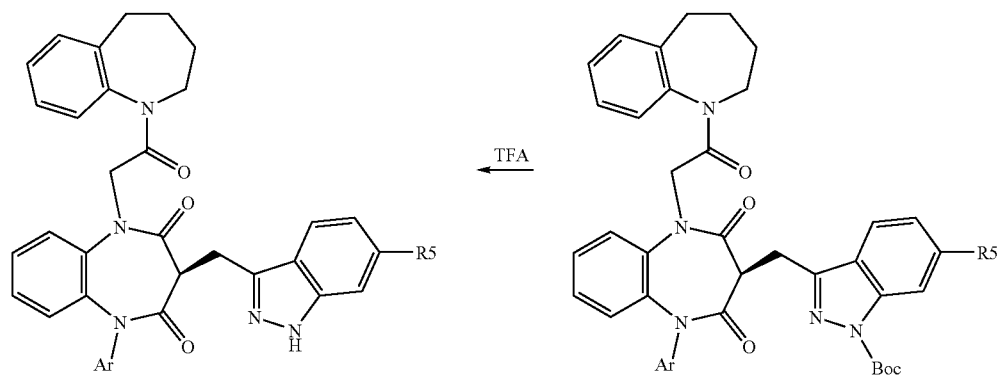

Second Preparation

Method B Thus compounds of Formula 1 may be prepared by reaction of a phenylenediamine with t-butylbromoacetate yielding compound (g) which upon treatment with malonyl dichloride provided benzodizepinedione (h). Compound (h) was treated with acid providing acid (i), which was esterified to give benzyl ester (j). Alkylation with bromomethylindazole afforded benzodiazepine (k). Benzyl ester was removed by hydrogenolysis and formed acid (l) was converted to acid chloride which reacted with benzoazepine (b) yielding compounds (f) which upon treatment with acid formed compound formula I.

Alternatively benzyl ester was separated using chiral column separation and steps k-l-f to compound Formula I were done on chiral material providing pure enantiomer of compound of Formula I.

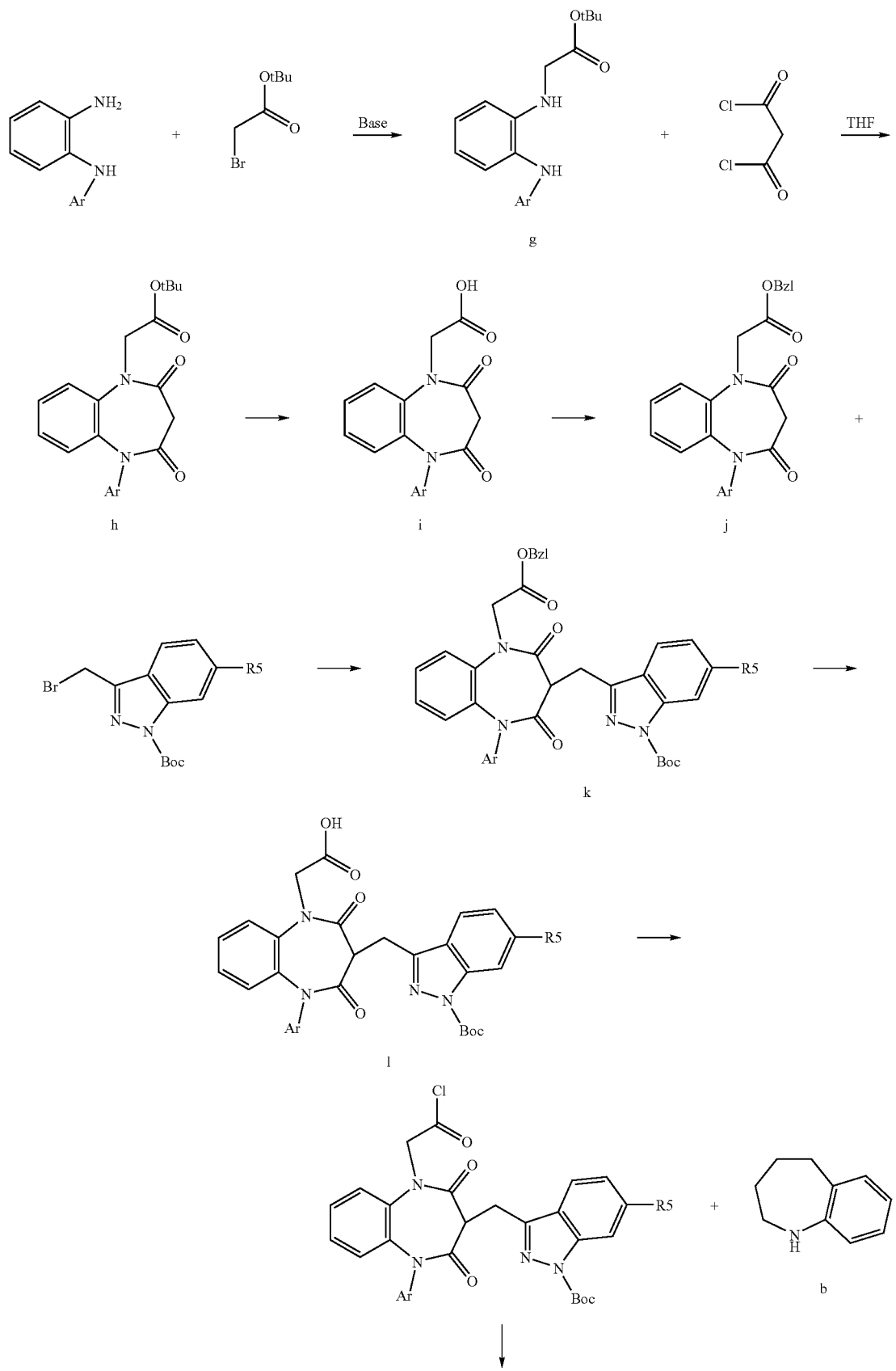

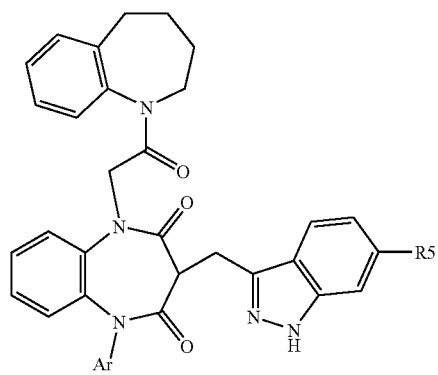

Formula I

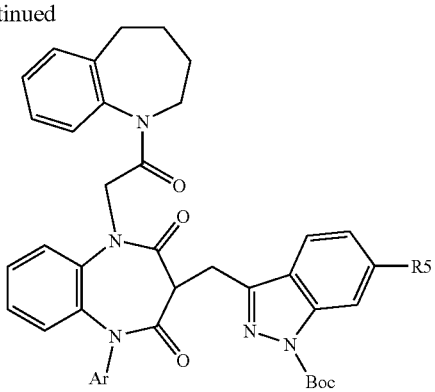

f

← TFA

EXAMPLES

The following examples are intended for illustration only and are not intended to limit the scope of the invention in any way, the invention being defined by the claims.

Reagents are commercially available or are prepared according to procedures in the literature.

Example 1

3-(1H-indazol-3-ylmethyl)-1-[2-oxo-2-(2,3,4,5-tetrahydro-1H-1-benzazepin-1-yl)ethyl]-5-phenyl-1H-1,5-benzodiazepine-2,4(3H,5H)-dione Method A Intermediate 1a (1Z)-3,4-dihydronaphthalen-1(2H)-one oxime To a solution of α-tetralone (50 g, 45.5 mL, 342 mmol) in anhydrous methanol (500 mL) was added hydroxylamine hydrochloride (24.7 g, 377 mmol) and sodium carbonate monohydrate (45 g, 363 mmol). The resulting slurry was stirred at ambient temperature for 36 h and the solvent was removed. The residue was titurated with water and the resulting solid was recrystallized from ether/hexanes to supply the product (37.1 g) as greenish tan crystals.

$^1$H NMR (300 MHz, CDCl$_3$) 8.41 (s, 1H); 7.85 (d, J=7.5 Hz, 1H); 7.10-7.28 (m, 2.68-2.85 (m, 4H); 1.80-1.91 (m, 2H).

Intermediate 1aa 1,3,4,5-tetrahydro-2H-1-benzazepin-2-one

Under nitrogen atmosphere, (1Z)-3,4-dihydronaphthalen-1(2H)-one oxime (0.500 g) in CH$_2$Cl$_2$ (10 ml) was added to polyphosphoric acid (~10 g). The mixture was heated to 60° C. under slight positive N2 flow. After the CH$_2$Cl$_2$ had evaporated, the mixture was heated to 80° C. for 1 hr. The reaction was quenched by slow addition of water then extracted with CH$_2$Cl$_2$ (3×20 ml). The combined extracts were dried with Na$_2$SO$_4$ then concentrated in vacuo to give 0.450 g of the titled product. $^1$H NMR (300 MHz, CDCl$_3$) 2.28 (m, 2H), 2.40 (m, 2H), 2.85 (t, J=7.14 Hz), 7.03 (d, J=7.70 Hz, 1H), 7.18 (m, 1H), 7.27 (d, J=7.28 Hz, 2H), 7.98 (bs, 1H). MS: ES+, m/z 162 [M+H]+.

Intermediate 1b 2,3,4,5-Tetrahydro-1H-benzo[b]azepine

Under anhydrous conditions and N2 atmosphere, 1,3,4,5-tetrahydro-2H-1-benzazepin-2-one (100 mg) in THF (5 ml) was treated with LiAlH4 (0.65 ml @ 1.0M in THF). The resulting solution was heated at reflux for 1 hr. The reaction was quenched by addition to a small amount of ice. The resulting mixture was diluted with a large excess of CH$_3$CN (~50:1) and filtered. The filtrate was concentrated in vacuo to give 84 mg of the titled product. $^1$H NMR (300 MHz, CDCl$_3$) 1.69 (m, 2H), 1.86 (m, 2H), 2.82 (m, 2H), 3.10 (m, 2H), 3.6 (bs, 1H), 6.80 (d, J=7.8 Hz, 1H), 6.88 (t, J=7.3 Hz, 1H), 7.09 (dt, J=7.6 Hz, J=1.4 Hz, 1H), 7.15 (d, J=7.4 Hz, 1H).

Intermediate 1c 1-(bromoacetyl)-2,3,4,5-tetrahydro-1H-1-benzazepine

To a 0° C. solution of 2,3,4,5-Tetrahydro-1H-benzo[b]azepine (5.5 g, 37.4 mmol) and triethylamine (5.21 mL, 37.4 mmol) in anhydrous methylene chloride (180 mL) under N$_2$ was added dropwise bromoacetyl bromide (3.25 mL, 37.4 mmol). The mixture was stirred at 0° C. for 2 h, then allowed to warm to ambient temperature and stirred for 1 h. The mixture was worked up by washing with 0.5 M aq. HCl (100 mL) and brine (100 mL). The organic layer was separated, dried over Na$_2$SO$_4$, filtered and concentrated to give the crude product as a brown semi-solid. Trituration with ether gave the product (5.69 g) as a tan solid.

$^1$H NMR (300 MHz, CDCl$_3$) 7.24–7.33 (m, 4H); 4.62–4.82 (m, 1H); 3.80 (d, J=10.7 Hz, 1H); 3.71 (d, J=10.7 Hz, 1H); 2.85–3.10 (m, 1H); 2.60–2.75 (m, 2H); 1.90–2.15 (m, 2H); 1.75–1.90 (m, 1H); 1.35–1.55 (m, 1H)

Intermediate 1d

N$^1$-[2-oxo-2-(2,3,4,5-tetrahydro-1H-1-benzazepin-1-yl)ethyl]-N$^2$-phenylbenzene-1,2-diamine To a stirring solution of N-phenyl-o-phenylene diamine (10 g, 54.3 mM) in 100 ml of DMF at RT was added K$_2$CO$_3$ (8.25 g, 60 mM) followed by 1-(bromoacetyl)-2,3,4,5-tetrahydro-1H-1-benzazepine (14.56 g 54.3 mM). The resulting mixture was stirred at RT until TLC (Hex:AcOEt 3:1)

showed completion of reaction. The mixture was filtered to remove the $K_2CO_3$ and then diluted with 800 mL of EtOAc and 200 mL of $Et_2O$. This solution was washed successively with $H_2O$ (2×400 mL), brine (1×400 mL), 1 N HCl (2×400 mL), and $H_2O$ (1×400 mL), and the organics dried ($MgSO_4$) and concentrated to give a greenish-black oil. The resultant oil was purified by silica gel flash column chromatography using hexane/EtOAc4/1 and the combined filtrates evaporated in vacuo to give 20 g of product. 1H NMR (300 MHz, CDCl3) 1.25–1.40 (m, 1H), 1.66–2.00 (m, 3H), 2.55.2.75 (m, 2H), 2.88 (t, J=13 Hz, 1H), 3.54(d, J=17 Hz, 1H), 4.10 (d, J=17 Hz, 1H), 4.57 (m, 1H), 6.80–7.80 (m, 12H), 7.47 (m, 1H).

Intermediate 1e

1-[2-oxo-2-(2,3,4,5-tetrahydro-1H-1-benzazepin-1-yl)ethyl]-5-phenyl-1H -1,5-benzodiazepine-2,4(3H, 5H)-dione To 100 mL of THF at 0° C. was added dropwise over 20 min simultaneously a solution of 8.0 g of the $N^1$-[2-oxo-2-(2,3,4,5-tetrahydro-1H-1-benzazepin-1-yl)ethyl]-$N^2$-phenylbenzene-1,2-diamine (8.0 g, 21.5 mM) in 100 mL of THF and solution of malonyl dichloride (2.40 mL, 25.8 mM) in 100 mL of THF. The resulting solution was stirred at RT for 20 h and the solvent removed in vacuo. The resultant material was purified by silica gel flash column chromatography using hexanes/EtOAc 1/1 and the combined filtrates evaporated in vacuo to give 7.5 g of product.

$^1$H NMR (400 MHz, $CDCl_3$) 7.58 (d, 8.2 Hz, 1H); 7.16–7.42 (m, 10H); 7.06–7.12 (m, 1H); 6.87–6.93 (m, 1H); 4.71–4.80 (m, 2H); 4.22–4.38 (m, 1H); 3.59 (d, J=12 Hz, 1H); 3.47 (d, 12 Hz, 1H); 2.63–3.31 (m, 2H); 1.96–2.08 (m, 2H); 1.75–1.87 (m, 1H); 1.52–1.58 (m, 1H); 1.33–1.47 (m, 1H)

Intermediate 1f tert-butyl 3-({2,4-dioxo-1-[2-oxo-2-(2,3,4,5-tetrahydro-1H-1-benzazepin-1-yl)ethyl]-5-phenyl-2,3,4,5-tetrahydro-1H-1,5-benzodiazepin-3-yl}methyl)-1H-indazole-1-carboxylate To a stirring solution of 1-[2-oxo-2-(2,3,4,5-tetrahydro-1H-1-benzazepin-1-yl)ethyl]-5-phenyl-1H-1,5-benzodiazepine-2,4(3H,5H)-dione (1.0 g, 2.28 mM) in 15 mL DMF at 0° C. was added 1.1 equiv. of 0.5 M solution of $KN(TMS)_2$ in toluene. The resulting solution was stirred 10–30 min, then a solution of tert-butyl 3-(bromomethyl)-1H-indazole-1-carboxylate (0.78 g, 2.5 mM) in 3 mL DMF was added. The resulting solution was stirred 2 h at RT and then quenched with 5 mL of $H_2O$. The reaction mixture was then poured into 50 mL of EtOAc and extracted with $H_2O$ (2×50 mL). The organic layer was separated, dried ($MgSO_4$), and the solvents removed in vacuo. The resultant material was purified by silica gel flash column chromatography using hexanes/EtOAc 1/1 providing 1.4 g of white solid.

$^1$H NMR (300 MHz, $CDCl_3$) 8.06–8.13 (m, 1H); 7.88–7.96 (m, 1H); 7.46–7.58 (m, 2H); 7.25–7.45 (m, 11H); 7.12–7.19 (m, 1H); 6.97–7.03 (m, 1H); 4.65–4.81 (m, 1H); 4.13–4.55 (m, 2H); 3.87–3.97 (m, 1H); 3.53–3.64 (m, 1H); 2.62–2.85 (m, 2H); 1.95–2.13 (m, 1H); 1.25–1.87 (m, 2H); 1.71 (s, 9H)

3-(1H-Indazol-3-ylmethyl)-1-[2-oxo-2-(2,3,4,5-tetrahydro-benzo[b]azepin-1-yl)-ethyl]-5-phenyl-1,5-dihydro-benzo[b][1,4]diazepine-2,4-dione A solution of tert-butyl 3-({2,4-dioxo-1-[2-oxo-2-(2,3,4,5-tetrahydro-1H-1-benzazepin -1-yl)ethyl]-5-phenyl-2,3,4,5-tetrahydro-1H-1,5-benzodiazepin-3-yl}methyl)-1H-indazole -1-carboxylate (800 mg) in methylene chloride (30 mL) was treated with trifluoroacetic acid (10 mL). The reaction was stirred for 45 minutes then concentrated to dryness. The residue was chromatographed on silica gel (Hexane:Ethyl Acetate) to yield 600 mg of white solid.

$^1$H NMR (300 MHz, DMSO-$D_6$) 7.74–7.83 (m, 1H); 7.28–7.61 (m, 13H); 7.19–7.27 (m, 1H)); 7.04–7.12 (m, 1H); 6.90–6.98 (m, 1H); 3.75–4.53 (m, 4H); 3.37–3.55 (m, 2H); 2.48–3.01 (m, 3H); 1.85–2.05 (m, 1H); 1.62–1.82 (m, 1H); 1.20–1.40 (m, 1H)

Active Enantiomer of Example 1

(R) or (S) 3-(1H-Indazol-3-ylmethyl)-1-[2-oxo-2-(2, 3,4,5-tetrahydrobenzo[b]azepin-1-yl)-ethyl]-5-phenyl-1,5-dihydro-benzo[b][1,4]diazepine-2,4-dione Racemic example 1 was separated on the Prochrom Preparative Supercritical Fluid Chromatograph Super C20

Column Chiralcel OJ (2×25 CM)

Temperature: 40 C

Pressure: 21 MPa

CO2 flow rate: 50 g/min

Mobile Phase: 13% Ethanol with 0.2% TEA at a flow rate of 6 ml/min 290 nm

Active compound eluted as second.

Purity was determine to be >98% by analytical chiral column.

Enantiomer of Intermediate 1f tert-butyl 3-({2,4-dioxo-1-[2-oxo-2-(2,3,4,5-tetrahydro-1H-1-benzazepin-1-yl)ethyl]-5-phenyl-2,3,4,5-tetrahydro-1H-1,5-benzodiazepin-3-yl}methyl)-1H-indazole -1-carboxylate Racemic example 1f was separated on the Prochrom Preparative Supercritical Fluid Chromatograph Super C20 on Regis (R,R) Whelk-O-1 (25 cm×2.11 cm), 40 C, 21 Mpa 44 g/min, 18 ml.minMeOH (10% Chloroform) 290 nm, 1.25 ml inj. 37.5 mg/injection.

Active Enantiomer of Example 1

(R) or (S) 3-(1H-Indazol-3-ylmethyl)-1-[2-oxo-2-(2, 3,4,5-tetrahydrobenzo[b]azepin-1-yl)-ethyl]-5-phenyl-1,5-dihydro-benzo[b][1,4]diazepine-2,4-dione A solution of enantiomer of tert-butyl 3-({benzodiazepin-3-yl}methyl)-1H-indazole-1-carboxylate (300 mg) in methylene chloride (10 mL) was treated with trifluoroacetic acid (10 mL). The reaction was stirred for 45 minutes then concentrated to dryness. The residue was chromatographed on silica gel (Hexane:Ethyl Acetate) to yield 200 mg of white solid. 2,4-dioxo-1-[2-oxo-2-(2,3,4,5-tetrahydro-1H-1-benzazepin-1-yl)ethyl]-5-phenyl-2,3,4,5-tetrahydro-1H-1,5-

Racemic Intermediate 1f tert-butyl 3-({2,4-dioxo-1-[2-oxo-2-(2,3,4,5-tetrahydro-1H-1-benzazepin-1-yl)ethyl]-5-phenyl-2,3,4,5-tetrahydro-1H-1,5-benzodiazepin-3-yl}methyl)-1H-indazole-1-carboxylate To a solution of enantiomer 1 (inactive) of tert-butyl 3-({2,4-dioxo-1-[2-oxo-2-(2,3,4,5-tetrahydro-1H-1-benzazepin-1-yl)ethyl]-5-phenyl-2,3,4,5-tetrahydro-1H-1,5-benzodiazepin-3-yl}methyl)-1H-indazole-1-carboxylate (200 mg) in 5 ml of DMF 50 mg of DBU was added and mixture was stirred overnight. Chiral HPLC:
Supercritical Fluid Chromatograph Super C20 on Regis (R,R) Whelk-O-1; 30% MeOH, 2 ml/min.

Example 2

3-(1H-indazol-3-ylmethyl)-1-[2-(7-methoxy-2,3,4,5-tetrahydro-1H-1-benzazepin -1-yl)-2-oxoethyl]-5-phenyl-1H-1,5-benzodiazepine-2,4(3H,5H)-dione Method B Intermediate 2a (1Z)-5-methoxy-3,4-dihydronaphthalen-1 (2H)-one oxime A solution of 6-methoxy-1-tetralone (5.0 g) in ethanol (100 mL) was treated with hydroxylamine hydrochloride (2.0 g) and sodium carbonate (3.6 g). The reaction mixture was heated overnight at 80° C. Cooled to room temperature after twenty hours, transferred to a 300 mL flask and concentrated. The residue was triturated in water and filtered to yield the title product as a brown solid (5.3 g) $^1$H NMR (400 MHz, CDCl$_3$) 1.84–1.87(m, 2H), 2.72(t, J=6.2 Hz, 2H), 2.79(t, J=6.6 Hz, 2H), 3.80(s, 3H), 6.65(d, J=2.6 Hz, 1H), 6.76(dd, J=11.5, 2.7 Hz, 1H), 7.86 (d, J=8.8 Hz, 1H)

Intermediate 2b 7-methoxy-2,3,4,5-tetrahydro-1H-1-benzazepine

The 6-methoxy-3,4-dihydronaphthalen-1(2H)-one (2.5 g) in anhydrous methylene chloride (148 mL) was cooled to 0° C. and treated with diisobutylaluminum hydride (1.0M in hexane, 58.3 mL). After stirring for 1.5 hours sodium fluoride (11.0 g) was added to the reaction mixture. Water (4 mL) was added dropwise and stirred for 15 minutes. Celite was added and the mixture was stirred an additional 10 minutes. The reaction was filtered and concentrated to yield a residue. Dissolved in Hexane:Ethyl Ether (1:1, 50 mL) and stirred with aqueous Rochelle's salt (75 mL) for 1.25 hours. Extracted aqueous layer with Hexane:Ethyl Ether (1:1, 50 mL). Combine organic layers, dried over sodium sulfate, filtered and concentrated to yield the title compound as a yellow oil (1.47 g) $^1$H NMR (400 MHz, CDCl$_3$) 1.60–1.62 (m, 2H), 1.77–1.79(m, 2H), 2.71–2.74(m, 2H), 2.96–2.98 (m, 2H), 3.74(s, 3H), 6.56–6.59 (m, 1H), 6.67–6.69 (m, 2H)

Intermediate 2q tert-butyl N-(2-anilinophenyl)glycinate

To a stirring solution of N-phenyl-o-phenylene diamine (20 g, 180.55 n M) in 200 ml of DMF at RT was added K$_2$CO$_3$ (16.5 g, 120 mM) followed by tert-butyl bromoacetate (21.17 g 108.55 mM). The resulting mixture was stirred at RT until TLC (Hex:AcOEt 3:1) showed completion of reaction. The mixture was filtered to remove the K$_2$CO$_3$ and then diluted with 800 mL of EtOAc and 200 mL of Et$_2$O. This solution was washed successively with H$_2$O (2×400 mL), brine (1×400 mL), 1 N HCl (2×400 mL), and H$_2$O (1×400 mL), and the organics dried (MgSO$_4$) and concentrated to give a greenish-black oil. The resultant oil was purified by silica gel flash column chromatography using hexane/EtOAc 4/1 and the combined filtrates evaporated in vacuo to give 30 g of product.

Intermediate 2h tert-butyl (2,4-dioxo-5-phenyl-2,3,4,5-tetrahydro-1H-1,5-benzodiazepin-1-yl)acetate To 100 mL of THF at 0° C. was added dropwise over 20 min simultaneously a solution of the tert-butyl N-(2-anilinophenyl)glycinate (9.5 g, 31.8 mM) in 100 mL of THF and solution of malonyl dichloride (5.38 mL, 38.21 mM) in 100 mL of THF. The resulting solution was stirred at RT for 20 h and the solvent removed in vacuo. The resultant material was purified by silica gel flash column chromatography using hexanes/EtOAc 6/14 and the combined filtrates evaporated in vacuo to give 10.2 g of product. 1H NMR (DMSO-d6) 1.40 (s, 9H), 3.19 (d, J=12 Hz, 1H), 3.69 (d, J=12 Hz, 1H), 4.55 (d, J=17 Hz, 1H), 4.71 (d, J=17 Hz, 1H), 6.89 (d, J=8 Hz, 1H), 7.20 (t, J=8 Hz, 1H), 7.33 (m, 4H), 7.46 (m, 3H).

Intermediate 2i (2,4-dioxo-5-phenyl-2,3,4,5-tetrahydro-1H-1,5-benzodiazepin-1-yl)acetic acid tert-butyl (2,4-dioxo-5-phenyl-2,3,4,5-tetrahydro-1H-1,5-benzodiazepin-1-yl)acetate (9.5 g, 25.9 mM) was dissolved in 200 ml of 4N HCl in dioxane and stirred overnight. Solvent was evaporated under reduced pressure providing 7.8 g of product.

Intermediate 2j benzyl (2,4-dioxo-5-phenyl-2,3,4,5-tetrahydro-1H-1, 5-benzodiazepin-1-yl)acetate (2,4-dioxo-5-phenyl-2,3,4,5-tetrahydro-1H-1,5-benzodiazepin-1-yl)acetic acid (8.0 g, 25.78 mM) and benzyl alcohol (3.35 g, 31 mM) were dissolved in 200 ml of toluene and 0.5 g of p-toluenesulfonic acid were added and resulting mixture was refluxed until TLC (Hexane/AcOEt 8/12) showed completion of reaction. Organic layer was washed 3 times with sodium bicarbonate solution, dried and toluene evaporated providing 9.5 g of product.

Intermediate 2k tert-butyl 3-({1-[2-(benzyloxy)-2-oxoethyl]-2,4-dioxo-5-phenyl-2,3,4,5-tetrahydro-1H-1,5-benzodiazepin-3-yl}methyl)-1H-indazole-1-carboxylate To a stirring solution of benzyl (2,4-dioxo-5-phenyl-2,3, 4,5-tetrahydro-1H-1,5-benzodiazepin-1-yl)acetate (3.45 g, 8.62 mM) in 25 mL DMF at 0° C. was added 1.1 equiv. of 0.5 M solution of KN(TMS)$_2$ in toluene. The resulting solution was stirred 10–30 min, then a solution of tert-butyl 3-(bromomethyl)-1H-indazole-1-carboxylate (2.95 g, 9.48 mM) in 15 mL DMF was added. The resulting solution was stirred 2 h at RT and then quenched with 5 mL of $H_2O$. The reaction mixture was then poured into 50 mL of EtOAc and extracted with $H_2O$ (2×50 mL). The organic layer was separated, dried ($MgSO_4$), and the solvents removed in vacuo. The resultant material was purified by silica gel flash column chromatography using methylene chloride/EtOAc 9/1 providing 4.4 g of white solid.

$^1$H NMR (300 MHz, $CDCl_3$) 8.04 (d, J=8.2 Hz, 1H); 7.92 (d, J=8.2 Hz, 1H); 7.11–7.35 (m, 15H); 6.97–7.12(m, 1H); 5.17 (s, 2H); 4.93 (d, J=7.5 Hz, 1H); 4.61 (d, J=7.5 Hz, 1H); 4.35–4.41 (m, 1H); 3.58–3.88 (m, 2H); 1.67 (s, 9H).

Intermediate 21

{3-[(1-methyl-1H-indazol-3-yl)methyl]-2,4-dioxo-5-phenyl-2,3,4,5-tetrahydro-1H -1,5-benzodiazepin-1-yl}acetic acid tert-butyl 3-({1-[2-(benzyloxy)-2-oxoethyl]-2,4-dioxo-5-phenyl-2,3,4,5-tetrahydro-1H -1,5-benzodiazepin-3-yl}methyl)-1H-indazole-1-carboxylate (0.6 g, 0.95 mM) were dissolved in 10 ml of ethyl acetate and 50 mg of 10% Pd/C were added. Reaction mixture was hydrogenated at atm. Pressure overnight. Catalyst was removed by filtration and was solvent evaporated under reduced pressure. 0.44 g of product was obtained.

Intermediate 2m tert-butyl 3-({1-[2-(7-methoxy-2,3,4,5-tetrahydro-1H-1-benzazepin-1-yl)-2-oxoethyl]-2,4-dioxo-5-phenyl-2,3,4,5-tetrahydro-1H-1,5-benzodiazepin-3-yl}methyl)-1H-indazole-1-carboxylate A solution of (3-{[1-(tert-butoxycarbonyl)-1H-indazol-3-yl]methyl}-2,4-dioxo-5-phenyl-2,3,4,5-tetrahydro-1H-1,5-benzodiazepin-1-yl)acetic acid (60 mg) in methylene chloride (2 mL) was cooled to 0° C. Anhydrous dimethylformamide (1 drop) then oxalyl chloride (166 μL) were added and the reaction stirred for 1 hour. The reaction was concentrated to yield the acid chloride as foam. During this time 7-methoxy-2,3,4,5-tetrahydro-1H-1-benzazepine (58.5 mg) was dissolved in methylene chloride (1 mL) and cooled to 0° C. in a separate flask. The acid chloride was dissolved in methylene chloride (1 mL) and syringed into the benzazepine/methylene chloride mixture. Stirred at 0° C. for 1 hour then partitioned between saturated aqueous sodium bicarbonate and ethyl acetate. The organic layer was dried over sodium sulfate, filtered and concentrated to yield a yellow oil. Chromatographed on silica gel (Hexane:Ethyl Acetate) to yield the title compound as a clear oil (47 mg).

Electrospray MS (positive ion): (M+H) 699.84, (M+Na) 721.8

(negative ion): (M−H) 697.80

3-(1H-indazol-3-ylmethyl)-1-[2-(7-methoxy-2,3,4,5-tetrahydro-1H-1-benzazepin -1-yl)-2-oxoethyl]-5-phenyl-1H-1,5-benzodiazepine-2,4(3H,5H)-dione A solution of tert-butyl 3-({1-[2-(7-methoxy-2,3,4,5-tetrahydro-1H-1-benzazepin-1-yl) -2-oxoethyl]-2,4-dioxo-5-phenyl-2,3,4,5-tetrahydro-1H-1,5-benzodiazepin-3-yl}methyl) -1H-indazole-1-carboxylate (47 mg) in methylene chloride (10 mL) was treated with trifluoroacetic acid (1 mL). The reaction was stirred for 45 minutes then concentrated to dryness. The residue was chromatographed on silica gel (Hexane:Ethyl Acetate) to yield a foamy oil. The foam was triturated with Ethyl Ether and filtered to yield the title compound as a white solid (12 mg).

$C_{36}H_{33}N_5O_4Na$: MNa+ calcd 622.2430, found 622.2450 Δ2.0 mmu;

TLC Rf (1:1 Hexane/Ethyl Acetate)=0.30 mp: 215–230° C.

Example 3

1-[2-(6,8-dimethyl-2,3,4,5-tetrahydro-1H-1-benzazepin-1-yl)-2-oxoethyl]-3(1H-indazol-3-ylmethyl)-5-phenyl-1H-1,5-benzodiazepine-2,4(3H,5H)-dione Intermediate 3a 5,7-dimethyl-3,4-dihydronaphthalen-1(2H)-one oxime A solution of 5,7-Dimethyl-1-tetralone (5.0 g) in ethanol (100 mL) was treated with hydroxylamine hydrochloride (2.2 g) and sodium carbonate monohydrate (3.6 g). The reaction mixture was heated overnight at 80° C. with a condenser and behind a blast shield. Cooled to room temperature after seventeen hours, transferred to a 300 mL flask and concentrated. The residue was triturated in water and filtered to yield the title product as a beige solid (5.1 g).

H-NMR: (400 MHz, $CDCl_3$) 1.83–1.89(m, 2H), 2.23(s, 3H), 2.28(s, 3H), 2.64(t, J=6.2 Hz, 2H), 2.78(t, J=6.7 Hz, 2H), 7.00 (s, 1H), 7.62(s, 1H)

Intermediate 3b 6,8-dimethyl-2,3,4,5-tetrahydro-1H-1-benzazepine

The 5,7-dimethyl-3,4-dihydronaphthalen-1 (2H)-one (2.5 g) in anhydrous methylene chloride (150 mL) was cooled to 0° C. and treated with diisobutylaluminum hydride (1.0M in hexane, 57.8 mL). After stirring for 2 hours sodium fluoride (11.0 g) was added to the reaction mixture. Water (5 mL) was added dropwise and stirred for 3 hours. Reintroduced ice bath because solvent was evaporating. Celite was added and the reaction was stirred, filtered and concentrated to yield a yellow solid. Chromatographed on silica gel (Hexane:Ethyl Acetate) to yield the title compound as a white solid.

1H-NMR: (400 MHz, $CDCl_3$) 1.54–1.59 (m, 2H), 1.73-1.79 (m, 2H), 2.18 (s, 3H), 2.24 (s, 3H), 2.70–2.75 (m, 2H), 2.99–3.02 (m, 2H), 6.44 (s, 1H), 6.56 (s, 1H).

Intermediate 3m tert-butyl 3-({1-[2-(6,8-dimethyl-2,3,4,5-tetrahydro-1H-1-benzazepin-1-yl)-2-oxoethyl]-2,4-dioxo-5-phenyl-2,3,4,5-tetrahydro-1H-1,5-benzodiazepin-3-yl}methyl)-1H-indazole-1-carboxylate A solution of (3-{[1-(tert-butoxycarbonyl)-1H-indazol-3-yl]methyl}-2,4-dioxo-5-phenyl -2,3,4,5-tetrahydro-1H-1,5-benzodiazepin-1-yl)acetic acid (120 mg) in methylene chloride (4 mL) was cooled to 0° C. Anhydrous dimethylformamide (1 drop) then oxalyl chloride (332μΛ) were added and the reaction stirred for 1 hour. The reaction was concentrated to yield the acid chloride as a yellow foam. During this time 6,8-dimethyl-2,3,4,5-tetrahydro-1H-1-benzazepine (54.5 mg) was dissolved in methylene chloride (1 mL) and cooled to 0° C. The acid chloride was dissolved in methylene chloride (2 mL) and 1 mL of the solution was added to the benzazepine/methylene chloride solution. Stirred for 1.25 hours and partitioned between saturated aqueous sodium bicarbonate and Ethyl Acetate. The organic layer was dried over sodium sulfate, filtered and concentrated to yield a yellow oil. The oil was chromatographed on silica gel (Hexane:Ethyl Acetate) to yield the title compound as a yellow oil (64 mg).

Electrospray MS (positive ion) (M+H) 698.33, (M+Na) 720.37

1-[2-(6,8-dimethyl-2,3,4,5-tetrahydro-1H-1-benzazepin-1-yl)-2-oxoethyl]-3-(1H-indazol-3-ylmethyl)-5-phenyl-1H-1,5-benzodiazepine-2,4(3H,5H)-dione A solution of tert-butyl 3-({1-[2-(6,8-dimethyl-2,3,4,5-tetrahydro-1H-1-benzazepin-1-yl)-2-oxoethyl]-2,4-dioxo-5-phenyl-2,3,4,5-tetrahydro-1H-1,5-benzodiazepin-3-yl}methyl)-1H-indazole-1-carboxylate (64 mg) in methylene chloride (10 mL) was treated with trifluoroacetic acid (1 mL). The reaction was stirred for 3 hours then concentrated to dryness. The residue was chromatographed on silica gel (Hexane:Ethyl Acetate. The residue was triturated with Ethyl Ether and filtered to yield the title compound as an off-white solid (7 mg).

$C_{37}H_{35}N_5O_3Na$: MNa+ calcd 620.2638, found 620.2638 Δ0.0 mmu;

TLC Rf: (1:1 Hexane/Ethyl Acetate)=0.50

Example 4

3-(1H-indazol-3-ylmethyl)-1-[2-(6-methoxy-2,3,4,5-tetrahydro-1H-1-benzazepin-1-yl)-2-oxoethyl]-5-phenyl-1H-1,5-benzodiazepine-2,4(3H,5H)-dione Intermediate 4a 5-methoxy-3,4-dihydronaphthalen-1(2H)-one oxime A solution of 5-methoxy-1-tetralone (5.0 g) in ethanol (100 mL) was treated with hydroxylamine hydrochloride (2.1 g) and sodium carbonate monohydrate (3.6 g). The reaction mixture was heated overnight at 80° C. with a condenser. Cooled to room temperature after approximately seventeen hours, transferred to another flask and concentrated. The residue was triturated in water and filtered to yield the title product as a beige solid (5.1 g).

1H-NMR: (400 MHz, CDCl$_3$) 1.78–1.85(m, 2H), 2.70(t, J=6.2 Hz, 2H), 2.76(t, J=6.7 Hz, 2H), 3.80(s, 3H), 6.80 (d, J=8.0 Hz, 1H), 7.13(t, J=8.1 Hz, 1H), 7.50(d, J=8.1 Hz)

Intermediate 4b 6-methoxy-2,3,4,5-tetrahydro-1H-1-benzazepine

The 5-methoxy-3,4-dihydronaphthalen-1 (2H)-one (2.5 g) in anhydrous methylene chloride (150 mL) was cooled to 0° C. and treated with diisobutylaluminum hydride (1.0M in hexane, 57.2 mL). After stirring for 2 hours sodium fluoride (10.9 g) was added to the reaction mixture. Water (5 mL) was added dropwise and stirred for two hours. Reintroduced ice bath because solvent was evaporating. Celite was added and the reaction was stirred, filtered and concentrated to yield a yellow solid. Chromatographed on silica gel (Hexane:Ethyl Acetate) to yield the title compound as a yellow oil (1.45 g).

1H-NMR: (400 MHz, CDCl$_3$) 1.55–1.60(m, 2H), 1.73–1.78(m, 2H), 2.80–2.83(m, 2 H), 3.01–3.04(m, 2H), 3.76(s, 3H), 6.36(d, J=7.9 Hz, 1H), 6.43(d, J=8.2 Hz, 1 H), 6.93(t, J=8.0 Hz, 1H).

Intermediate 4m tert-butyl 3-({1-[2-(6-methoxy-2,3,4,5-tetrahydro-1H-1-benzazepin-1-yl)-2-oxoethyl]-2,4-dioxo-5-phenyl-2,3,4,5-tetrahydro-1H-1,5-benzodiazepin-3-yl}methyl)-1H-indazole-1-carboxylate A solution of (3-{[1-(tert-butoxycarbonyl)-1H-indazol-3-yl]methyl}-2,4-dioxo-5-phenyl-2,3,4,5-tetrahydro-1H-1,5-benzodiazepin-1-yl)acetic acid (120 mg) in methylene chloride (4 mL) was cooled to 0° C. Anhydrous dimethylformamide (1 drop) then oxalyl chloride (322 μL) were added and the reaction stirred for 1 hour. The reaction was concentrated to yield the acid chloride as a yellow foam. During this time 6-methoxy-2,3,4,5-tetrahydro-1H-1-benzazepine (58.5 mg) was dissolved in methylene chloride (1 mL) and cooled to 0° C. The acid chloride was dissolved in methylene chloride (2 mL) and 1 mL of the solution was added to the benzazepine/methylene chloride solution. Stirred for 2.5 hours and partitioned between saturated aqueous sodium bicarbonate and Ethyl Acetate. The organic layer was dried over sodium sulfate, filtered and concentrated to yield a yellow oil. The oil was chromatographed on silica gel (Hexane:Ethyl Acetate) to yield the title compound as a yellow oil (83 mg).

Electrospray MS (Positive Ion): (M+H) 700.00, (M+Na) 721.94

3-(1H-indazol-3-ylmethyl)-1-[2-(6-methoxy-2,3,4,5-tetrahydro-1H-1-benzazepin-1-yl)-2-oxoethyl]-5-phenyl-1H-1,5-benzodiazepine-2,4(3H,5H)-dione A solution of tert-butyl 3-({1-[2-(6-methoxy-2,3,4,5-tetrahydro-1H-1-benzazepin-1-yl)-2-oxoethyl]-2,4-dioxo-5-phenyl-2,3,4,5-tetrahydro-1H-1,5-benzodiazepin-3-yl}methyl)-1H-indazole-1-carboxylate (83 mg) in methylene chloride (10 mL) was treated with trifluoroacetic acid (1 mL). The reaction was stirred overnight then concentrated to dryness. The residue was chromatographed on silica gel (Hexane:Ethyl Acetate. The residue was triturated with Ethyl Ether and filtered to yield the title compound as a white powder (14 mg).

$C_{36}H_{33}N_5O_4Na$: MNa+ calcd 622.2430, found 620.2419 Δ1.1 mmu;

Assay found C, 66.23, H, 5.21, N, 10.40; $C_{36}H_{33}N_5O4.0.5C_2HO_2F_3.0.75H_2O$ requires C66.31, H, 5.26, N, 10.45.

Example 5

(3R)-3-(1H-indazol-3-ylmethyl)-1-[2-(6-methoxy-2, 3,4,5-tetrahydro-1H-1-benzazepin-1-yl)-2-oxoethyl]-5-phenyl-1H-1,5-benzodiazepine-2,4(3H,5H)-dione Intermediate 5a 5-methoxy-3,4-dihydronaphthalen-1(2H)-one oxime A solution of 5-methoxy-1-tetralone (5.0 g) in ethanol (100 mL) was treated with hydroxylamine hydrochloride (2.1 g) and sodium carbonate monohydrate (3.6 g). The reaction mixture was heated overnight at 80° C. with a condenser. Cooled to room temperature after approximately seventeen hours, transferred to another flask and concentrated. The residue was triturated in water and filtered to yield the title product as a beige solid (5.1 g).

1H-NMR: (400 MHz, CDCl$_3$) 1.78–1.85(m, 2H), 2.70(t, J=6.2 Hz, 2H), 2.76(t, J=6.7 Hz, 2H), 3.80(s, 3H), 6.80 (d, J=8.0 Hz, 1H), 7.13(t, J=8.1 Hz, 1H), 7.50(d, J=8.1 Hz)

Intermediate 5b 6-methoxy-2,3,4,5-tetrahydro-1H-1-benzazepine

The 5-methoxy-3,4-dihydronaphthalen-1 (2H)-one (2.5 g) in anhydrous methylene chloride (150 mL) was cooled to 0° C. and treated with diisobutylaluminum hydride (1.0M in hexane, 57.2 mL). After stirring for 2 hours sodium fluoride (10.9 g) was added to the reaction mixture. Water (5 mL) was added dropwise and stirred for two hours. Reintroduced ice bath because solvent was evaporating. Celite was added and the reaction was stirred, filtered and concentrated to yield a yellow solid. Chromatographed on silica gel (Hexane:Ethyl Acetate) to yield the title compound as a yellow oil (1.45 g).

1H-NMR: (400 MHz, CDCl$_3$) 1.55–1.60(m, 2H), 1.73–1.78(m, 2H), 2.80–2.83(m, 3.01–3.04(m, 2H), 3.76(s, 3H), 6.36(d, J=7.9 Hz, 1H), 6.43(d, J=8.2 Hz, 1H), 6.93(t, J=8.0 Hz, 1H).

Intermediate 5m tert-butyl 3-({(3R)-1-[2-(6-methoxy-2,3,4,5-tetrahydro-1H-1-benzazepin-1-yl)-2-oxoethyl]-2,4-dioxo-5-phenyl-2,3,4,5-tetrahydro-1H-1,5-benzodiazepin-3-yl}methyl)-1H-indazole-1-carboxylate A solution of ((3R)-3-{[1-(tert-butoxycarbonyl)-1H-indazol-3-yl]methyl}-2,4-dioxo-5-phenyl-2,3,4,5-tetrahydro-1H-1,5-benzodiazepin-1-yl)acetic acid (317 mg) in methylene chloride (5 mL) was cooled to 0° C. Anhydrous dimethylformamide (1 drop) then oxalyl chloride (880 µL) were added and the reaction stirred for 1 hour. The reaction was concentrated to yield the acid chloride as a yellow foam. During this time 6-methoxy-2,3,4,5-tetrahydro-1H-1-benzazepine (78 mg) was dissolved in methylene chloride (1 mL) and cooled to 0° C. The acid chloride was dissolved in methylene chloride (4 mL) and 1 mL of the solution was added to the benzazepine/methylene chloride solution. Stirred for 2 hours and partitioned between saturated aqueous sodium bicarbonate and Ethyl Acetate. The organic layer was dried over sodium sulfate, filtered and concentrated to yield an oil. The oil was chromatographed on silica gel (Hexane:Ethyl Acetate) to yield the title compound (93 mg).

Electrospray MS (positive ion): (M+H) 700.05, (M+Na) 722.01

(3R)-3-(1H-indazol-3-ylmethyl)-1-[2-(6-methoxy-2,3,4,5-tetrahydro-1H-1-benzazepin-1-yl)-2-oxoethyl]-5-phenyl-1H-1,5-benzodiazepine-2,4(3H,5H)-dione A solution of tert-butyl 3-({(3R)-1-[2-(6-methoxy-2,3,4,5-tetrahydro-1H-1-benzazepin-1-yl)-2-oxoethyl]-2,4-dioxo-5-phenyl-2,3,4,5-tetrahydro-1H-1,5-benzodiazepin-3-yl}methyl)-1H-indazole-1-carboxylate (93 mg) in methylene chloride (10 mL) was treated with trifluoroacetic acid (1 mL). Stirred for 1.25 hours and concentrated the solvent off. Chromatographed on silica gel (Hexane:Ethyl Acetate) then lyophilized to yield the title compound as a white film (64 mg).

TLC Rf=0.26 mp=186° C.–214° C.

Assay found C, 70.37, H, 5.52, N, 11.20; $C_{36}H_{33}N_5O_4 \cdot 0.80H_2O$ requires C70.41, 5.68, N, 11.40.

Example 6

(3R)-1-[2-(6,8-dimethyl-2,3,4,5-tetrahydro-1H-1-benzazepin-1-yl)-2-oxoethyl]-5-phenyl-3-(4,5,6,7-tetrahydro-1H-indazol-3-ylmethyl)-1H-1,5-benzodiazepine-2,4(3H,5H)-dione Intermediate 6a 5,7-dimethyl-3,4-dihydronaphthalen-1(2H)-one oxime A solution of 5,7-Dimethyl-1-tetralone (5.0 g) in ethanol (100 mL) was treated with hydroxylamine hydrochloride (2.2 g) and sodium carbonate monohydrate (3.6 g). The reaction mixture was heated overnight at 80° C. with a condenser and behind a blast shield. Cooled to room temperature after seventeen hours, transferred to a 300 mL flask and concentrated. The residue was triturated in water and filtered to yield the title product as a beige solid (5.1 g).

H-NMR: (400 MHz, CDCl$_3$) 1.83–1.89(m, 2H), 2.23(s, 3H), 2.28(s, 3H), 2.64(t, J=6.2 Hz, 2H), 2.78(t, J=6.7 Hz, 2H), 7.00 (s, 1H), 7.62(s, 1H)

Intermediate 6b 6,8-dimethyl-2,3,4,5-tetrahydro-1H-1-benzazepine

The 5,7-dimethyl-3,4-dihydronaphthalen-1(2H)-one (2.5 g) in anhydrous methylene chloride (150 mL) was cooled to 0° C. and treated with diisobutylaluminum hydride (1.0M in hexane, 57.8 mL). After stirring for 2 hours sodium fluoride (11.0 g) was added to the reaction mixture. Water (5 mL) was added dropwise and stirred for 3 hours. Reintroduced ice bath because solvent was evaporating. Celite was added and the reaction was stirred, filtered and concentrated to yield a yellow solid. Chromatographed on silica gel (Hexane:Ethyl Acetate) to yield the title compound as a white solid.

1H-NMR: (400 MHz, CDCl$_3$) 1.54–1.59 (m, 2H), 1.73-1.79 (m, 2H), 2.18 (s, 3H), 224(s, 3H), 2.70–2.75 (m, 2H), 2.99–3.02 (m, 2H), 6.44 (s, 1H), 6.56 (s, 1H).

Enantiomer of Intermediate 2k tert-butyl 3-({1-[2-(benzyloxy)-2-oxoethyl]-2,4-dioxo-5-phenyl-2,3,4,5-tetrahydro-1H-1,5-benzodiazepin-3-yl}methyl)-1H-indazole-1-carboxylate Racemic intermediate 2k was separated on the Prochrom Preparative Supercritical Fluid Chromatograph Super C20

Column Chiralcel OD (2×25 CM)

Temperature: 40 C

Pressure: 21 MPa

CO2 flow rate: 50 g/min

Mobile Phase: 10 ml of MeOH (10% chloroform) 47 g/min.

300 nm

Purity of both enantiomers was determine to be >98% by analytical chiral column.

Enantiomer of Intermediate 21

(S or R) (3-{[1-(tert-butoxycarbonyl)-1H-indazol-3-yl]methyl}-2,4-dioxo-5-phenyl-2,3,4,5-tetrahydro-1H-1,5-benzodiazepin-1-yl) acetic acid (0.3 g, 0.95 mM) of tert-butyl 3-({1-[2-(benzyloxy)-2-oxoethyl]-2,4-dioxo-5-phenyl-2,3,4,5-tetrahydro-1H-1,5-benzodiazepin-3-yl}methyl)-1H-indazole-1-carboxylate were dissolved in 10 ml of ethyl acetate and 50 mg of 10% Pd/C were added. Reaction mixture was hydrogenated at atm. Pressure overnight. Catalyst was removed by filtration and was solvent evaporated under reduced pressure. 0.22 g of product was obtained.

Intermediate 6m tert-butyl 3-({(3R)-1-[2-(6,8-dimethyl-2,3,4,5-tetrahydro-1H-1-benzazepin-1-yl)-2-oxoethyl]-2,4-dioxo-5-phenyl-2,3,4,5-tetrahydro-1H-1,5-benzodiazepin-3-yl}methyl)-1H-indazole-1-carboxylate A solution of ((3R)-3-{[1-(tert-butoxycarbonyl)-1H-indazol-3-yl]methyl}-2,4-dioxo-5-phenyl-2,3,4,5-tetrahydro-1H-1,5-benzodiazepin-1-yl)acetic acid (800 mg) in methylene chloride (15 mL) was cooled to 0° C. Anhydrous dimethylformamide (2 drops) then oxalyl chloride (2.2 mL) were added and the reaction stirred for 1 hour. The reaction was concentrated to yield the acid chloride as a yellow foam. During this time 6,8-dimethyl-2,3,4,5-tetrahydro-1H-1-benzazepine (202.4 mg) was dissolved in methylene chloride (2 mL) and cooled to 0° C. The acid chloride (276 mg) was dissolved in methylene chloride (2 mL) and 1 mL of the solution was added to the benzazepine/methylene chloride solution. Stirred for 3 hours to 0° C. and partitioned between saturated aqueous sodium bicarbonate and Ethyl Acetate. The organic layer was dried over sodium sulfate, filtered and concentrated to yield a brown foam. The foam was chromatographed on silica gel (Hexane:Ethyl Acetate) to yield the title compound as a white foam (304 mg).

Electrospray MS (positive ion): (M+H) 698.20, (M+Na) 720.15.

Intermediate 6n (3R)-1-[2-(6,8-dimethyl-2,3,4,5-tetrahydro-1H-1-benzazepin-1-yl)-2-oxoethyl]-3-(1H-indazol-3-ylmethyl)-5-phenyl-1H-1,5-benzodiazepine-2,4(3H,5H)-dione A solution of tert-butyl 3-{[(3R)-1-(2-chloro-2-oxoethyl)-2,4-dioxo-5-phenyl-2,3,4,5-tetrahydro-1H-1,5-benzodiazepin-3-yl]methyl}-1H-indazole-1-carboxylate (304 mg) in methylene chloride (10 mL) was treated with trifluoroacetic acid (1 mL) and stirred at room temperature for 4 hours. Concentrated solvent then partitioned between saturated aqueous sodium bicarbonate and chloroform. Dried the organic layer over sodium sulfate, filtered and concentrated to yield a white foam. Chromatographed on silica gel (chloroform:methanol) to obtain the title product as a white solid (157 mg).

Electrospray MS (positive ion): (M+H) 598.61

Example 6

(3R)-1-[2-(6,8-dimethyl-2,3,4,5-tetrahydro-1H-1-benzazepin-1-yl)-2-oxoethyl]-5-phenyl-3-(4,5,6,7-tetrahydro-1H-indazol-3-ylmethyl)-1H-1,5-benzodiazepine-2,4(3H,5H)-dione A solution of (3R)-1-[2-(6,8-dimethyl-2,3,4,5-tetrahydro-1H-1-benzazepin-1-yl)-2-oxoethyl]-3-(1H-indazol-3-ylmethyl)-5-phenyl-1H-1,5-benzodiazepine-2,4(3H,5H)-dione (50 mg) in ethyl acetate (8 mL) was treated with 10% palladium on charcoal (300 mg). Placed under $H_2$ environment (by balloon) and stirred at room temperature for 48 hours. Filtered through celite and concentrated to dryness. Chromatographed on silica gel (Hexane:Ethyl Acetate). Lyophilized the residue to yield the title compound as a white solid (6.6 mg)

$C_{37}H_{36}N_5O_3N$: MH+ calcd 602.3131, found 602.3120 Δ1.1 mmu;

TLC Rf: (100% Ethyl Acetate)=0.32

Example 7

(3R)-1-[2-(6-methoxy-2,3,4,5-tetrahydro-1H-1-benzazepin-1-yl)-2-oxoethyl]-5-phenyl-3-(4,5,6,7-tetrahydro-1H-indazol-3-ylmethyl)-1H-1,5-benzodiazepine-2,4(3H,5H)-dione A solution of (3R)-3-(1H-indazol-3-ylmethyl)-1-[2-(6-methoxy-2,3,4,5-tetrahydro-1H-1-benzazepin-1-yl)-2-oxoethyl]-5-phenyl-1H-1,5-benzodiazepine-2,4(3H,5H)-dione (32 mg) in ethyl acetate (4 mL) was treated with 10% palladium on charcoal (300 mg). Placed under $H_2$ environment (by balloon) and stirred at room temperature for 48 hours. Filtered through celite and concentrated to dryness. Chromatographed on silica gel (Hexane:Ethyl Acetate). Lyophilized the residue to yield the title compound as a white solid (5.3 mg)

$C_{36}H_{38}N_5O_4$: MH+ calcd 604.2924, found 604.2923 Δ0.1 mmu;

TLC Rf: (100% Ethyl Acetate)=0.37

Example 8

2-[3-(1H-indazol-3-ylmethyl)-3-methoxy-2,4-dioxo-5-pyridin-3-yl-2,3,4,5-tetrahydro-1H-1,5-benzodiazepin-1-yl]-N-isopropyl-N-(4-methoxyphenyl)acetamide Compound was prepared as described in J. Med. Chem 40, 2706–2725 (1997)

Example 9

Enantiomer 1 2-[3-(1H-indazol-3-ylmethyl)-3-methoxy-2,4-dioxo-5-pyridin-3-yl-2,3,4,5-tetrahydro-1H-1,5-benzodiazepin-1-yl]-N-isopropyl-N-(4-methoxyphenyl)acetamide 2-[3-(1H-indazol-3-ylmethyl)-3-methoxy-2,4-dioxo-5-pyridin-3-yl-2,3,4,5-tetrahydro -1H-1,5-benzodiazepin-1-yl]-N-isopropyl-N-(4-methoxyphenyl) acetamide was separated on Column Chiralpak AS (2×25 cm) from Chiral Technologies, 15 ml/min of EtOH (0.2% TEA), 45 g/min of CO2, 210 Bar, 40 C, 290 nm, 16.5 mg/inj providing enantiomer 1.

Example 10

Enantiomer 2 2-[3-(1H-indazol-3-ylmethyl)-3-methoxy-2,4-dioxo-5-pyridin-3-yl-2,3,4,5-tetrahydro-1H-1,5-benzodiazepin-1-yl]-N-isopropyl-N-(4-methoxyphenyl)acetamide 2-[3-(1H-indazol-3-ylmethyl)-3-methoxy-2,4-dioxo-5-pyridin-3-yl-2,3,4,5-tetrahydro -1H-1,5-benzodiazepin-1-yl]-N-isopropyl-N-(4-methoxyphenyl) acetamide was separated on Column Chiralpak AS (2×25 cm) from Chiral Technologies, 15 ml/min of EtOH (0.2% TEA), 45 g/min of CO2, 210 Bar, 40 C, 290 nm, 16.5 mg/inj providing enantiomer 2.

Example 11

3-(1H-indazol-3-ylmethyl)-3-methoxy-1-[2-oxo-2-(2,3,4,5-tetrahydro-1H-1-benzazepin-1-yl)ethyl]-5-phenyl-1H-1,5-benzodiazepine-2,4(3H,5H)-dione Following procedures described in J. Med. Chem., 1997, 40 (17), pp. 2706–2725, the title compound was isolated as a white powder. $^1$H NMR (DMSO-D6): δ 1.45–1.76 (m, 4H), 3.00 (m, 2H), 3.38 (s, 3H), 3.81–3.93 (m, 2H), 4.26 (m, 2H), 4.52 (m, 2H), 6.71 (m, 1H), 7.02–7.51 (m, 15H), 7.95 (m, 1H). LCMS m/z=600 (MH+), 622 (M+Na+).

Example 12

3-[(6-fluoro-1H-indazol-3-yl)methyl]-1-[2-oxo-2-(2,3,4,5-tetrahydro-1H-1-benzazepin-1-yl)ethyl]-5-phenyl-1H-1,5-benzodiazepine-2,4(3H,5H)-dione Obtained using Method A $^1$H NMR (300 MHz, DMSO-D$_6$) 7.74–7.83 (m, 1H); 7.28–7.61 (m, 13H); 7.19–7.27 (m, 1H)); 6.90–6.98 (m, 1H); 3.75–4.53 (m, 4H); 3.37–3.55 (m, 2H); 2.48–3.01 (m, 3H); 1.85–2.05 (m, 1H); 1.62–1.82 (m, 1H); 1.20–1.40 (m, 1H) MS (ESI) [M+H]$^+$=588.

Biological Data

Biological data for compounds of the invention useful as MC4R agonists is set forth in Table 2.

Reporter Gene Assay

CHO-6×CRE-luc$^+$ reporter cell lines expressing human MC1R, MC3R, MC4R, and MC5R (GenBank accession numbers X65634, LO6155, S77415 and U08353) and the CHO host reporter gene cell line were propagated in complete medium in T225 flasks. Forty-eight hours prior to assay, cells were harvested with 2 ml of 0.05% trypsin, washed with complete medium and plated at a concentration of 4000 cells/well in complete medium. Sixteen hours prior to the assay, the medium was removed from the cells and replaced with 90 μl/well of serum-free DMEM/F12. At the time of the assay the compounds were added in a 10 μl volume and plates were incubated for 4 h at 37° C. in a cell culture incubator. The medium was aspirated followed by the addition of 50 μl of a 1:1 mixture of LucLite™ and dPBS containing 1 mM CaCl$_2$ and 1 mM MgCl$_2$. The plates were then sealed and subjected to dark adaptation at room temperature for 10 min before luciferase activity was quantitated on a TopCount™ microplate scintillation counter (Packard) using 3 s/well count time. The NDP-αMSH and 154N-5 concentration-response curve data were expressed as a percentage of the fold stimulation in the NDP-αMSH control for each receptor subtype. The control value is the average of duplicate wells treated with 1×10$^{-7}$ M NDP-αMSH.

TABLE 2

| Example # | pEC$_{50}$ | % of MSH |
| --- | --- | --- |
| 1 | 6.51 | 60 |
| 2 | 6.54 | 42 |
| 3 | 7.22 | 47 |
| 4 | 6.75 | 45 |
| 5 | 6.55 | 44 |
| 6 | 6.59 | 35 |
| 7 | 6.80 | 41 |
| 8 | 6.60 | 74 |
| 9 | 6.80 | 68 |
| 10 | 6.70 | 29 |
| 11 | 6.95 | 59 |
| 12 | 6.76 | 52 |

The application of which this description and claims forms part may be used as a basis for priority in respect of any subsequent application. The claims of such subsequent application may be directed to any novel feature or combination of features described herein. This may take the form of product, composition, process or use claims any include, by way of example and without limitation, one or more of the following claims.

What is claimed is:

1. A compound having the formula

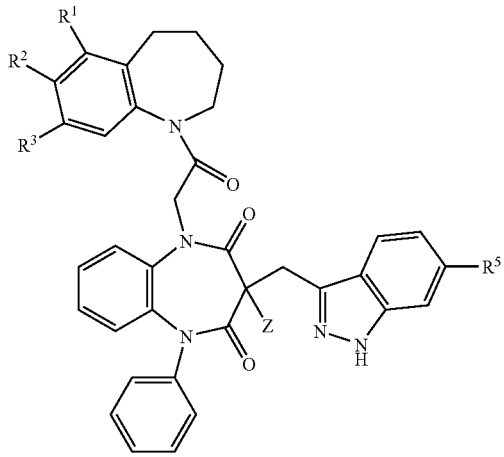

IB wherein Z is —H or a C$_1$–C$_6$ alkoxy; each R$^1$, R$^2$, and R$^3$ is independently selected from the group consisting of hydrogen, a C$_1$–C$_6$ alkyl, a C$_1$–C$_6$ alkoxy, and hydroxy; and R$^5$ is selected from hydrogen and fluorine.

2. A pharmaceutical composition comprising a compound according to claim 1 or a physiologically acceptable salt thereof and one or more pharmaceutically acceptable excipients.

3. A method of treatment of a MC4R disorder comprising administering to said mammal a therapeutically effective amount of a pharmaceutical composition according to claim 2, wherein the MC4R disorder is obesity.

* * * * *